(12) United States Patent
Kitano et al.

(10) Patent No.: US 6,191,328 B1
(45) Date of Patent: Feb. 20, 2001

(54) METHOD FOR 1, 1, 1, 3, 3-PENTAFLUOROPROPANE

(75) Inventors: Keisuke Kitano; Tatsuo Nakada; Takashi Shibanuma, all of Osaka (JP)

(73) Assignee: Daikin Industries, Ltd., Osaka (JP)

( * ) Notice: Under 35 U.S.C. 154(b), the term of this patent shall be extended for 0 days.

(21) Appl. No.: 09/202,824

(22) PCT Filed: Jun. 19, 1997

(86) PCT No.: PCT/JP97/02102

§ 371 Date: Dec. 22, 1998

§ 102(e) Date: Dec. 22, 1998

(87) PCT Pub. No.: WO97/49656

PCT Pub. Date: Dec. 31, 1997

(30) Foreign Application Priority Data

Jun. 27, 1996 (JP) .................................... 8-167440

(51) Int. Cl.⁷ .................................................. C07C 17/38
(52) U.S. Cl. ........................................................ 570/180
(58) Field of Search ................................ 570/180, 134

(56) References Cited

U.S. PATENT DOCUMENTS

| | | |
|---|---|---|
| 3,071,628 | 1/1963 | Linch . |
| 3,873,629 | 3/1975 | Jones . |
| 5,684,219 * | 11/1997 | Boyce et al. ........................... 570/180 |
| 5,874,658 * | 2/1999 | Belter .................................... 570/180 |
| 5,973,215 * | 10/1999 | Belter .................................... 570/180 |
| 6,013,846 * | 1/2000 | Wismer et al. ....................... 570/180 |

FOREIGN PATENT DOCUMENTS

| | | |
|---|---|---|
| 0353970 | 2/1990 | (EP) . |
| 0703205 | 3/1996 | (EP) . |
| 0729932 | 9/1996 | (EP) . |
| 0885863 | 12/1998 | (EP) . |
| 5-178768 | 7/1993 | (JP) . |
| 5-279277 | 10/1993 | (JP) . |
| 8-104655 | 4/1996 | (JP) . |
| 9-002983 | 1/1997 | (JP) . |
| 92983 | 1/1997 | (JP) . |
| 110738 | 4/1997 | (JP) . |
| 9-110738 | 4/1997 | (JP) . |

\* cited by examiner

*Primary Examiner*—Alan Siegel
(74) *Attorney, Agent, or Firm*—Birch, Stewart, Kolasch &Birch, LLP

(57) ABSTRACT

HFC-245fa is effectively separated from the mixture comprising 1,1,1,3,3-pentafluoropropane (HFC-245fa) and HF through a purification process comprising contacting at least one extraction agent selected from the group consisting of (a) a compound corresponds to the general formula (I): $C_xF_yH_z$, (b) a compound corresponds to the general formula (II): $R_1R_2R_3N$, (c) an compound corresponds to the general formula (III): $R_4OR_5$ and (d) a compound corresponds to the general formula (IV): $C_lCl_mH_n$ with a mixture comprising 1,1,1,3,3-pentafluoropropane and hydrogen fluoride so as to form a liquid mixture and separating the liquid mixture into two liquid layers, followed by obtaining an extraction agent phase including HFC-245fa and the extraction agent as the main components, and separatively recovering HFC-245fa from the extraction agent phase.

9 Claims, 1 Drawing Sheet

METHOD FOR 1, 1, 1, 3, 3-PENTAFLUOROPROPANE

This application is the national phase under 35 U.S.C. §371 of prior PCT International Application No. PCT/JP97/02102 which has an International filing date of Jun. 19, 1997 which designated the United States of America.

FIELD OF THE INVENTION

The present invention relates to a process of purification of 1,1,1,3,3-pentafluoropropane (hereinafter, also referred to as HFC-245fa) which is useful as an alternative fluorocarbons for use in foaming agents.

BACKGROUND OF THE INVENTION

As a process of producing of HFC-245fa, a process is known in which 1,1,1,3,3-pentachloropropane is fluorinated with hydrogen fluoride (hereinafter, also referred to as HF) in the presence of several catalysts in either vapor phase or liquid phase.

In such a process to obtain HFC-245fa, it is necessary to recover HFC-245fa by removing HF from the product since unreacted HF generally remains in the reaction product in addition to HFC-245fa. In such case, HF is simultaneously required to be recovered and recycled to the reaction system from the economical viewpoint. However, HFC-245fa is found to form an azeotropic mixture with HF, which was disclosed in, for example, Japanese Patent Application No. 9085/1997 and Japanese Patent Kokai Application No. 156701/1997 both filed by us. We also found that it is difficult to recover HFC-245fa substantially free of HF through a simple distillation since the composition of such azeotropic mixture varies depending on the pressure, for example, the azeotropic mixture contains 55% by mole of HF at a pressure of 5 atm. In addition, it is not commercially easy to recover HFC-245fa solely without recovering such a large amount of HF.

As processes for separating fluorohydrocarbon compounds from HF, several processes, for example, a process to let each component of the mixture separate from each other to form two liquid layers and recover each component by distillation (Japanese Patent Kokai Publication No. 167803/1990); a process to use sulfuric acid as an extraction agent for HF (U.S. Pat. No. 3,873,629) and a process to remove HF through absorption into hydrofluoric acid (also referred to an aqueous HF solution) (Japanese Patent Kokai Publication No. 279277/1993) are known. Further, it is also known to successively distillate the mixture with two distillation columns in which the internal pressures are different each other, using a property that the composition of the azeotropic mixture varies depending on the pressure as disclosed in Japanese Patent Kokai Publication No. 178768/1993.

DISCLOSURE OF THE INVENTION

The process disclosed in the Japanese Patent Kokai Publication No. 167803/1990 can not be applied to any mixture since the process has to utilize a mixture each component of which separates from each other in liquid phase. The separating process using sulfuric acid has a disadvantage that it shows a strong corrosiveness when it is heated to a high temperature during recovery of HF.

In the separation process using aqueous HF solution, it is a severe disadvantage that the hydrofluoric acid has corrosiveness. For example, frequent check and maintenance of the equipment and lines are required, so that personal cost increases, in addition, the cost of installation also increases because the material to be used in such installation should be selected to have an anti-corrosiveness.

Therefore, an object of the present invention is to provide a process to obtain 1,1,1,3,3-pentafluoropropane (HFC-245fa) through effective separation of 1,1,1,3,3-pentafluoropropane from a mixture comprising at least 1,1,1,3,3-pentafluoropropane and hydrogen fluoride.

A major feature of the present invention is that HFC-245fa is effectively separated from a mixture comprising at least 1,1,1,3,3-pentafluoropropane and hydrogen fluoride by utilizing the following organic compounds (a)–(d) having a property that, on the one hand, they have a good compatibility with HFC-245fa, on the other hand, they have a poor compatibility with HF. In other word, the present invention provides a process to separate HFC-245fa from a mixture comprising at least 1,1,1,3,3-pentafluoropropane and hydrogen fluoride by utilizing a principle that, although the mixture of HFC-245fa and HF does not directly separate into the two liquid layers of each compound, HFC-245fa may be extracted into an extraction agent phase by using the extraction agent as mentioned above.

Concretely, the present invention provides a purification process of 1,1,1,3,3-pentafluoropropane characterized by contacting at least one extraction agent selected from the group consisting of (a) a fluorohydrocarbon compound corresponds to the general formula (I):

$$C_xF_yH_z \quad (I)$$

in which x is an integer from 3 to 10, y is an integer from 2 to 22 and z is an integer from 0 to 6;

(b) an amine compound corresponds to the general formula (II):

$$R_1R_2R_3N \quad (II)$$

in which $R_1$, $R_2$ and $R_3$ are fluoroalkyl groups each having 1–10 carbon atoms, respectively, and $R_1$, $R_2$ and $R_3$ may have at most two hydrogen atoms (0, 1 or 2 hydrogen atoms), respectively;

(c) an ether compound corresponds to the general formula (III):

$$R_4OR_5 \quad (III)$$

in which $R_4$ and $R_5$ are alkyl groups each having 1–10 carbon atoms, respectively, and at least one of $R_4$ and $R_5$ contains one fluorine atom; and (d) a chlorohydocarbon compound corresponds to the general formula (IV):

$$C_lCl_mH_n \quad (IV)$$

in which l is an integer from 3 to 10, m is an integer from 2 to 22 and n is an integer from 0 to 6 with a mixture comprising 1,1,1,3,3-pentafluoropropane and hydrogen fluoride so as to form a liquid mixture and separating the liquid mixture into two liquid layers, followed by obtaining an extraction agent layer including 1,1,1,3,3-pentafluoropropane and the extraction agent as main compounds, and separatively recovering 1,1,1,3,3-pentafluoropropane from the extraction agent layer.

Brief Description of Drawings

In FIG. 1, reference numbers denote the following elements, respectively:

Figure 1:
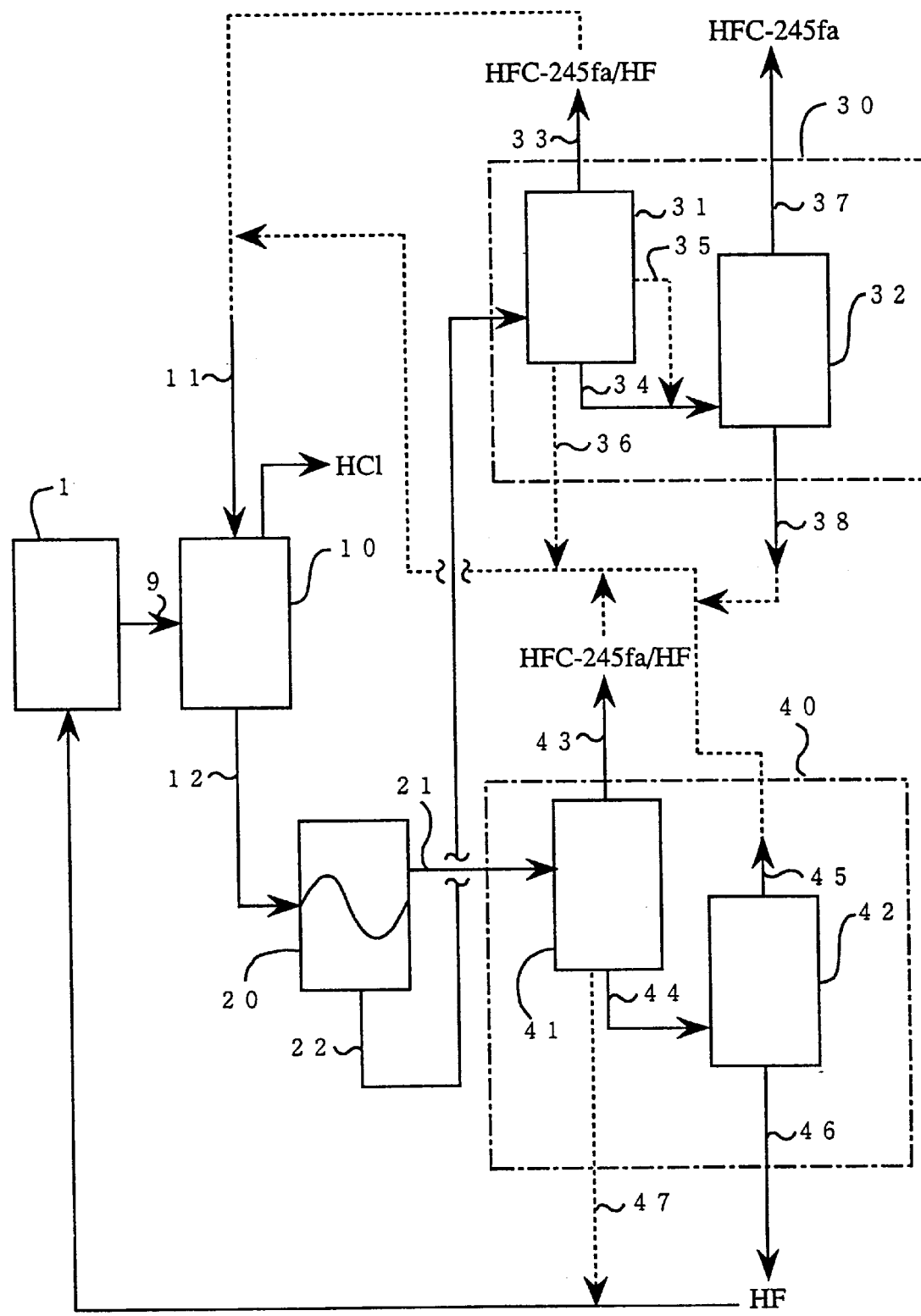
FIG. 1 shows a flow sheet of one embodiment of the present process.

1. reaction apparatus
9. conduit
10. extraction apparatus
11,12. conduit
20. separation apparatus
21,22. conduit
30. distillation measure
31,32. distillation apparatus
33,34,35,36,37. conduit
40. HF recovery measure
41,42. distillation apparatus
43,44,45,46,47. conduit The extraction agent used in the present invention may be any compound selected from the group consisting of the above mentioned (a), (b), (c) and (d) or a combination of two or more selected from the above group. Further, the extraction agent may contain another compound provided that it might not cause substantially detrimental effect to the present separative recovery process.

In the context of the present invention, the term "mixture" means a material comprising at least HFC-245fa and HF, which exists in liquid and/or gaseous phase. Optionally, it may contain HCl or the other fluorohydrocarbon compounds, for example, 1,1,1,3-tetrafluoro-3-chloropropane ($CF_3CH_2CHFCl$), 1,1,1-trifluoro-3,3-dichloropropane ($CF_3CH_2CHCl_2$) or 1,1-difluoro-1,3,3-trichloropropane ($ClCF_2CH_2CHCl_2$).

In the context of the present invention, the term "separative recovery" means to obtain a mixture containing HFC-245fa and HF in a higher rario of HFC-245fa/HF (that is, relative ratio of HFC-245fa to HF) than that ratio in the mixture containing HFC-245fa and HF from the mixture as the starting material.

In the context of the present invention, the term "extraction agent" means a material which has a function that, when the mixture exists in a gas phase or a liquid phase containing a gas, the extraction agent being contacted with the mixture liquefies the mixture to form a liquid mixture comprising HFC-245fa and HF, and then selectively dissolves and extracts HFC-245fa from the mixture, simultaneously dissolves HF as little as possible, that is, to let HF be in a separated phase (or layer) other than the extraction agent phase (or layer). Optionally, a portion of the mixture may be withdrawn as a gas outside of the system during the above liquefaction step. The extraction agent may have a function to selectively absorb HFC-245fa from the mixture followed by liquefying it (that is, HF forms another liquid phase (or layer) in stead of being extracted into the extraction agent) in addition to the above mentioned function or alternatively.

Therefore, the "extraction agent" of the present invention means a material which leads to form at least two separated liquid phases (or layers), wherein one phase (or layer) contains HF in a large proportion (hereinafter, also referred to as HF phase) and the another phase (or layer) contains HF in a small proportion (which phase contains HFC-245fa and extraction agent as its main component (hereinafter, also referred to as extraction agent phase)) by contacting with the mixture. HCl which may be contained within the mixture may be removed in a gas phase without at least a portion thereof being liquefied.

In the present invention, the ratio of HFC-245fa/HF in the extraction agent phase is larger than that of the mixture as the starting material after the extraction agent was contacted with the mixture comprising HFC-245fa and HF followed by forming the separated two liquid layers of HF phase (or layer) and the extraction agent phase (or layer). Thus, in this case, "separative recovery" according to the present invention as above mentioned may be said to be substantially accomplished, apart from finally separating HFC-245fa from the extraction agent phase.

The examples of the extraction agent which may be used in the present invention are as follows:

(a) The fluorohydrocarbon compound may be perfluoro-2-methylpentane (sec-$C_6F_{14}$), perfluoro-n-hexane (n-$C_6F_{14}$), 43-10mee(1,1,1,2,2,3,4,5,5,5-decafluoropentane), 1H-perfluoro-2-pentene, perfluoro-2-methyl-2-pentene, perfluoro-4-methyl-2-pentene, 1H-perfluorooctane (ω)-H perfluorooctane ($C_8F_{17}H$)), ω-H perfluorohexane($C_6F_{13}H$), perfluorocyclohexane, perfluoroheptane, perfluoropropane, perfluorobutane, pentadecafluoroheptane, and perfluorodecalin.

(b) The amine compound may be perfluorotributylamine, perfluoropentylamine, and perfluoro-N-methyl-morpholine.

(c) The ether compound may be methyl-1,1,2,3,3,3-hexafluoropropylether, ethyl-1,1,2,3,3,3-hexafluoropropylether and propyl-1,1,2,3,3,3-hexafluoropropylether, 1-methoxy-nonafluorobutane, and 1-ethoxy-nonafluorobutane.

(d) The chlorohydocarbon compound may be 1,1,1,3,3-pentachloropropane, hexachloropropane, trichloroethylene, and perchloroethylene.

The amount of the extraction agent to be used in the present invention may be in such a range that, when the extraction agent is contacted with the mixture at the operating condition, particularly at a temperature above −30° C., the amount of HFC-245fa actually contacts with the extraction agent is smaller than the amount of HFC-245fa which may be dissolved in the extraction agent, and the ratio of the amount of the extraction agent to the amount of the mixture is in a range in which the extraction agent liquid phase and HF liquid phase are easily separated from each other. Concretely, the amount of the extraction agent to be used is 0.3 times or more in a molar ratio, preferably in the range from 0.3 to 30 times, most preferably in the range from 1 to 5 times based on the amount of HFC-245fa in the mixture to be contacted with. In the most cases, the extraction agent phase (or layer) generally forms the lower layer and the HF phase (or layer) generally forms the upper layer in the separating apparatus. However, the extraction agent phase (or layer) does not always form the lower layer, but instead it may form the upper layer depending on the kind of the extraction agent used as well as the proportion of HFC-245fa contained within the extraction agent phase.

After separated, the extraction agent phase contains HF in the amount of the solubility thereof as a small amount component. Such HF may be removed from the extraction agent phase through conventional after-treatments, for example, alkaline washing or distillation in the subsequent treatment steps performed depending on the necessity. Thus, a mixture substantially consisting of HFC-245fa and extraction agent may be obtained. Further, this mixture may be subjected to a conventional separation treatment, for example distillation to obtain the aimed product HFC-245fa containing substantially no extraction agent. In another way, the extraction agent phase may be directly distilled, optionally in combination with several distillation treatments by selecting the operating condition suitably to obtain HFC-245fa not including both HF and extraction agent. Such separation treatments through the distillation are conventional.

The condition of the temperature and the pressure during the contact process is not limited provided that, after the mixture is liquefied, HFC-245fa is mainly extracted into the extraction agent phase, and HF is mainly extracted into the HF phase, or the mixture is distributed into the extraction agent phase and the HF phase based on the liquid—liquid equilibrium relationship under the operation condition after the mixture was absorbed into the extraction agent phase and/or HF phase, or the above both phenomena may be occurred at the same time.

The conditions at which the extraction agent and the mixture are separated into the liquid phases are not particularly limited provided that the extraction agent phase (or layer) may be separated from the mixture in liquid in the condition. Therefore, it may be the same condition as described as to contact process in the above. In a practicable condition, both in the contacting process and separating process, the temperature is maintained in a range from −30° C. to 150° C., preferably from −30° C. to 100° C., more preferably from −30° C. to 50° C. The pressure (absolute pressure) is maintained in a range above an atmospheric pressure (1 atm), preferably from 1 to 30 atm.

Hereinafter, one embodiment of the present invention will be explained in detail with reference to FIG. 1.

In the reaction apparatus 1, 1,1,1,3,3-pentafluoropropane is produced by fluorination of a starting material, for example, 1,1,1,3,3-pentachloropropane with hydrogen fluoride in vapor phase or liquid phase in the presence of a catalyst. The effluent from this reaction step is a mixture mainly containing 1,1,1,3,3-pentafluoropropane and hydrogen fluoride and additionally containing HCl and the other fluorohydrocarbons which is a intermediate to 1,1,1,3,3-pentafluoropropane, for example, 1,1,1-trifluoro-3-chloro-2-propane, 1,1,1,3-tetrafluoro-3-chloropropane, 1,1,1-pentafluoro-3,3-dichloropropane and/or 1,1-difluoro-1,3,3-trichloropropane. The mixture is passed through a condenser and a distillation apparatus (both of them, not shown), and introduced into the extraction apparatus 10 via conduit 9. At this point, the mixture substantially consists of HFC-245fa and HF and optionally existing HCl. The extraction agent is introduced into the extraction apparatus 10 via conduit 11.

As the extraction apparatus 10, several apparatuses may be used, which are conventionally used for gas absorbing treatment or liquid—liquid extracting treatment, for example, packed column, spray column, scrubber, plate column, bubble column, mixing tank (e.g. mixer-settler). When an absorbing apparatus of a differential type is used, it is particularly preferred that the extraction agent flows countercurrenly to and contacts with the mixture.

When the extraction agent contacts with the mixture containing 1,1,1,3,3-pentafluoropropane and hydrogen fluoride in the extraction apparatus 10, substantially the whole HFC-245fa and HF are liquefied, and a portion thereof, beginning to separate into two liquid layers, is passed to a separation apparatus 20 via conduit 12. HCl, which is optionally contained in the mixture, may be eliminated from the extraction apparatus 10 in gaseous phase in most cases.

It is particularly preferred that the inside condition of the extraction apparatus 10 and the separation apparatus 20 is maintained in a practical condition, for example, in a temperature range from −30° C. to 50° C. and a pressure range from 1 atm to 4.5 atm.

For the separation process, conventional apparatus, for example, an apparatus in which two liquid phases separate into two layers due to the difference between the specific gravities may be used.

Alternatively, the extraction apparatus 10 and the separation apparatus 20 may be integrated into one apparatus.

The extraction agent and each liquefied component of the mixture, which were introduced through the conduit 12 and already begin to separate into two liquid layers, form two liquid layers in the separation apparatus 20, for example, a gravity type separation apparatus. A phase the main component of which is HF (HF phase) gathers to form the upper layer or phase and a phase the main component of which is HFC-245fa and the extraction agent (extraction agent phase) gathers to form the lower layer or phase.

The extraction agent phase forming the lower layer in the separation apparatus 20 is passed to a distillation measure 30, for example a distillation column via conduit 22. The extraction agent phase passing the conduit 22 mainly consists of the extraction agent and HFC-245fa, and additionally small amount of HF, as shown in Table 7 in Example part.

The distillation measure 30 practically may be two stage-distillation measure consisting of a combination of a first stage distillation apparatus 31 and a second stage distillation apparatus 32 as shown in FIG. 1. In such case, HF which is contained in the phase introduced via conduit 22 in a small amount may be eliminated in the first stage distillation apparatus 31. Concretely, in the first stage distillation apparatus 31, the azeotropic mixture HFC-245fa/HF is distilled to the top of the apparatus and recovered through the conduit 33, so that HF may be separated from the mixture of HFC-245fa and extraction agent to obtain a mixture of HFC-245fa and extraction agent as a bottom product. The azeotropic mixture HFC-245fa/HF removed from the conduit 33 is preferably recycled to the extraction apparatus 10 via conduit 11. The bottom liquid product is removed from the distillation apparatus 31 through the conduit 34, and then separated into HFC-245fa which is the aimed product (from the top of the apparatus) and the extraction agent (from the bottom of the apparatus) in the second stage distillation apparatus 32.

Alternatively, the mixture of HFC-245fa and extraction agent may be removed via the conduit 35 as a side cut in the distillation apparatus 31. In such a case, the extraction agent is removed from the apparatus at the bottom thereof via conduit 36, which may be recycled to the extraction apparatus 10.

HFC-245fa separated in the distillation apparatus 32 is removed via conduit 37 at the top of the apparatus and passed to suitable receiver or required after-treatment apparatus. On the other hand, the extraction agent which does not contain HFC-245fa is subjected to a suitable treatment as required before recycled to the extraction apparatus 10 via conduit 11 to be used as the extraction agent again.

As an alternative embodiment, for example, an alkaline washing measure including an after-treatment measure may be installed in the intermediate of the conduit 22 in order to eliminate HF contained in the extraction agent phase, which embodiment is not shown in the FIG. 1. The water entering into the extraction agent phase by the alkaline washing may be removed, for example, by a treatment in an after-treatment measure, for example an absorption tower or distillation measure installed downstream of the alkaline washing measure. Alternatively, the distillation step as the after-treatment measure may be installed within the distillation measure 30. In such a case, since the mixture of HFC-245fa and extraction agent is obtained after HF and water were removed, the first stage distillation apparatus 31 may be omitted so that the mixture may be passed to the preceding second stage distillation apparatus 32 and treated as above.

The HF phase which forms the upper layer in the separating apparatus 20 may be removed via conduit 21. Since the HF phase contains small amount of extraction agent and HFC-245fa as shown in Table 7 in Example part, it is passed to a suitable HF recovery measure 40 in order to recover HF not containing extraction agent and HFC-245fa.

As HF recovery measure 40, for example, a distillation apparatus may be used. Such an apparatus may be a two stage-distillation measure consisting of a combination of a first stage distillation apparatus 41 with a second stage distillation apparatus 42 as shown in FIG. 1. At first, a HF phase is separated into the azeotropic mixture of HFC-245fa/HF and the mixture of extraction agent/HF by distillation in the first stage distillation apparatus 41. The azeotropic mixture HFC-245fa/HF is removed via conduit 43 at the top of the apparatus and the mixture of extraction agent/HF is removed via conduit 44 at the bottom of the apparatus. The azeotropic mixture of HFC-245fa/HF may be subjected to a suitable treatment as required, followed by recycling to the extraction apparatus 10 via conduit 11. The mixture of extraction agent and HF may be distilled to separate the extraction agent from HF in the second stage distillation apparatus 42 via conduit 44, so that the extraction agent may be withdrawn from the top of the apparatus and the HF may be withdrawn from the bottom of the apparatus. Such HF recovered from the bottom of the apparatus of the second stage distillation apparatus 42 may be subjected to a suitable treatment as required, and then recycled to the reaction apparatus 1 again. The extraction agent may be recycled to the extraction apparatus 10 via conduit 11.

However, the sequence of the separation treatment in the HF recovery measure 40 does not necessarily follow the above explained one, but may be changed. For example, when the extraction agent has the highest boiling point among the components within the HF phase, the process may be operated so that the extraction agent is separated from the mixture of HF and HFC-245fa in the first stage, and then HF is separated from the mixture of HF and HFC-245fa in the second stage, which embodiment is not shown in FIG. 1. Further, the mixture of HF and HFC-245fa obtained from the first stage may be directly recycled into the reaction step or recovered and suitably used.

The extraction agent, the azeotropic mixture HFC-245fa/HF and HF separated as explained above may be respectively treated depending on the necessity, followed by recycling to anywhere within the system or withdrawing outside the system. For example, when it is recycled to anywhere within the system, the extraction agent is passed to the conduit 11 and/or the HF is passed to the fluorination step in the reaction apparatus 1. Alternatively, the HF phase may be directly recycled to the reaction system.

As the distillation apparatus, conventionally used apparatuses, for example packed column or plate column may be used and those skilled in the art may easily select the operation condition based on the system to be distilled. The present invention utilizes the azeotropic property of HF and HFC-245fa as disclosed in our foregoing application described in the above in the background of the invention part to obtain the azeotropic mixture of HFC-245fa/HF in the separation process.

The present invention was explained with reference to the case that the mixture consists of HF and HFC-245fa by way of example, however the mixture may contain the other components in addition to HF and HFC-245fa. When the mixture contains a material having a low solubility in the HF phase or in the extraction agent phase at the operation condition, such as HCl, such a material may be ejected to outside of the system via the extraction apparatus 10 as the gaseous phase. Therefore, the present invention may be performed as in the above explained case. The other components dissolvable into the both phases may be merely distributed into the extraction agent phase and the HF phase based on its property, so that the fact that the finally attained relative ratio of HFC-245fa to HF is larger than that of the original mixture through the present process is not varied. Therefore, the case that the mixture contains the other component is consequently included in the scope of the present invention.

Further, in a particular embodiment, the present invention uses 1,1,1,3,3-pentachloropropane as the extraction agent, which is also one of the principal starting material for the present aimed product, 1,1,1,3,3-pentafluoropropane, and satisfies the requirement as the extraction agent for the present invention as mentioned above.

In such case, the HF phase removed from the separating apparatus 20 via conduit 21 contains HF, 1,1,1,3,3-pentachloropropane, and HFC-245fa as a small amount component. Thus, the azeotropic mixture HFC-245fa/HF is withdrawn from the top of the apparatus 41 and 1,1,1,3,3-pentafluoropropane and HF are withdrawn from the bottom of the apparatus 41. Since these 1,1,1,3,3-pentafluoropropane and HF are the starting materials for the production of HFC-245fa, the obtained mixture of 1,1,1,3,3-pentachloropropane and HF may be directly recycled to the reaction apparatus 1 to further utilize as the starting material for producing 1,1,1,3,3-pentafluoropropane.

Accordingly, as explained above with reference to the embodiment using the extraction agent other than 1,1,1,3,3-pentachloropropane, the second stage distillation apparatus 42 as the HF recovery measure may be omitted, so that the cost of installation and the cost of operation may be reduced.

EXAMPLE

Using several compounds as the extraction agent, 1,1,1,3,3-pentafluoropropane was separated from the mixture consisting of 1,1,1,3,3-pentafluoropropane and hydrogen fluoride in a laboratory scale according to the present process.

Into a pipe made of fluorocarbon resin, one end of which being provided with a valve and the other end being plugged, the mixture of HFC-245fa (1,1,1,3,3-pentafluoropropane) and HF and the extraction agent were introduced in each given amount to form a feed mixture, shaken sufficiently and settled to let the liquid phases separate into two layers. The upper HF phase was absorbed by water and the lower extraction agent phase was absorbed by organic solvent. The amount of fluoride ion existing in the water was measured with a fluorine ion meter and the amount of HF was calculated. The proportion of the organic compounds was analyzed using a gas chromatograph and each amount of the extraction agent and HFC-245fa in each phase was obtained.

Several measurement were performed using several extraction agent as shown in the following Tables 1–6 (mixing temperature and separation temperature: 20° C.)

Example 1

As the extraction agent, perfluoro-2-methylpentane (sec-$C_6F_{14}$) was used.

TABLE 1

|  | feed mixture (g) | HF phase (g) | extraction agent phase (g) |
|---|---|---|---|
| HFC-245fa | 9.7 | 0.2 | 9.4 |
| HF | 1.5 | 1.4 | 0.1 |
| sec-$C_6F_{14}$ | 15.4 | 0.1 | 15.3 |
| ratio of HFC-245fa/HF | 6.5 | 0.1 | 94.0 |

To the mixture having the HFC-245fa/HF ratio which is almost the same composition with the azeotropic mixture, sec-$C_6F_{14}$ was added and let the mixture separate into two liquid layers. Accordingly, a result that the amount of HF distributed to the HF phase was about 14 times as much as that distributed to the extraction agent phase (1.4/0.1), while the amount of HFC-245fa distributed to the extraction agent phase was about 47 times as much as that distributed to the HF phase (9.4/0.2) was obtained. Further, it was found that the ratio HFC-245fa/HF in the extraction agent phase (9.4/0.1=94.0) is over 14 times (94.0/6.5=14.5) as much as that ratio in the feed mixture (9.70/1.50=6.5). Since the difference in the boiling point between HFC-245fa and sec-$C_6F_{14}$ existing in the extraction agent phase is over 40° C. and the two compounds do not make an azeotropic mixture, they may be easily separated from each other by distillation. Therefore, a satisfactory separative recovery may be performed by using perfluoro-2-methylpentane.

Example 2

As the extraction agent, perfluorohexane (n-$C_6F_{14}$) was used.

TABLE 2

|  | feed mixture (g) | HF phase (g) | extraction agent phase (g) |
|---|---|---|---|
| HFC-245fa | 12.4 | 4.5 | 7.9 |
| HF | 1.9 | 1.2 | 0.6 |
| n-$C_6F_{14}$ | 29.7 | 1.1 | 28.3 |
| ratio of HFC-245fa/HF | 6.5 | 3.8 | 13.2 |

A result that the amount of HF distributed to the HF phase was about 2 times as much as that distributed to the extraction agent phase (1.2/0.6), while the amount of HFC-245fa distributed to the extraction agent phase was about 2 times as much as that distributed to the HF phase (7.9/4.5) was obtained. Further, it was found that the ratio of HFC-245fa/HF in the extraction agent phase (7.9/0.6=13.2) is about 2 times as much as that ratio in the feed mixture (12.4/1.9=6.5). Therefore, a satisfactory separative recovery may be performed by using perfluorohexane.

Example 3

As the extraction agent, HFC-43-10mee was used.

TABLE 3

|  | feed mixture (g) | HF phase (g) | extraction agent phase (g) |
|---|---|---|---|
| HFC-245fa | 10.1 | 8.2 | 1.9 |

TABLE 3-continued

|  | feed mixture (g) | HF phase (g) | extraction agent phase (g) |
|---|---|---|---|
| HF | 1.5 | 1.4 | 0.1 |
| HFC-43-10mee | 15.0 | 4.5 | 10.5 |
| ratio of HFC-245fa/HF | 6.7 | 5.9 | 19.0 |

Using HFC-43-10mee as extraction agent, HF was found to be concentrated in HF phase about 14 times as much as that in the extraction agent phase. Since the HFC-245fa was extracted about one fifth the amount thereof into the extraction agent phase in one through procedure, HFC-245fa may be separated from HF by repeating the procedure and recycling the extraction agent. Further, the ratio of HFC-245fa/HF in the extraction agent phase (1.90/0.10=19.0) is about 2 times as much as that ratio in the feed mixture (10.1/1.50=6.7), so that a satisfactory separative recovery may be performed by using HFC-43-10mee.

Example 4

As the extraction agent, 1,1,1,3,3-pentachloropropane was used.

TABLE 4

|  | feed mixture (g) | HF phase (g) | extraction agent phase (g) |
|---|---|---|---|
| HFC-245fa | 12.3 | 8.8 | 3.5 |
| HF | 1.9 | 1.8 | 0.1 |
| 1,1,1,3,3-pentachloropropane | 12.5 | 3.8 | 8.6 |
| ratio of HFC-245fa/HF | 6.5 | 4.9 | 35.0 |

HF is concentrated in HF phase about 18 times as much as that in the extraction agent phase (1.8/0.1) and the HFC-245fa is extracted about three tenth the amount thereof into the extraction agent phase. Further, the ratio of HFC-245fa/HF in the extraction agent phase (3.5/0.1=35) is about 5 times as much as that ratio in the feed mixture (12.3/1.9=6.5). Therefore, a satisfactory separative recovery may be performed by using 1,1,1,3,3-pentachloropropane. An almost complete separation of HFC-245fa may be performed by successive recycling of the extraction agent.

Further, use of 1,1,1,3,3-pentachloropropane as the extraction agent, which is one of the starting material for the production of 1,1,1,3,3-pentafluoropropane in the present process to separate 1,1,1,3,3-pentafluoropropane from the mixture of 1,1,1,3,3-pentafluoropropane and HF means that a third component other than the two components of the starting materials never enters into the reaction system, so that the HF recovery measure is not required during the recycling HF in the HF phase obtained from the separation step, in this embodiment. Therefore, installation cost and operation cost may be reduced in the plant performing the present process.

Example 5

As the extraction agent, perfluorobutylamine (hereinafter, also referred to PFBA) was used.

TABLE 5

|  | feed mixture (g) | HF phase (g) | extraction agent phase (g) |
|---|---|---|---|
| HFC-245fa | 10.2 | 5.0 | 5.2 |
| HF | 1.5 | 1.0 | 0.5 |
| PFBA | 15.1 | 3.1 | 12.0 |
| ratio of HFC-245fa/HF | 6.8 | 5.0 | 10.4 |

HF is extracted in HF phase about 2 times as much as that in the extraction agent phase (1.0/0.5) and the HFC-245fa is extracted almost half of the fed amount (5.2/10.2). In addition, the ratio of HFC-245fa/HF in the extraction agent phase (5.2/0.5=10.4) is about 1.5 times as much as that ratio in the feed mixture (10.2/1.5=6.8). Therefore, a satisfactory separative recovery may be performed by using perfluorobutylamine and almost complete separation of HFC-245fa may be performed by successive recycling of the extraction agent.

Example 6

As the extraction agent, methyl-1,1,2,3,3,3-hexafluoropropylether (hereinafter, referred to FPE) was used.

TABLE 6

|  | feed mixture (g) | HF phase (g) | extraction agent phase (g) |
|---|---|---|---|
| HFC-245fa | 10.0 | 4.1 | 5.9 |
| HF | 1.5 | 1.0 | 0.5 |
| FPE | 15.0 | 3.0 | 12.0 |
| ratio of HFC-245fa/HF | 6.7 | 4.1 | 11.8 |

HF is extracted in HF phase about 2 times as much as that in the extraction agent phase (1.0/0.5) and the HFC-245fa is extracted almost six tenth of the fed amount (5.9/10.0). In addition, the ratio of HFC-245fa/HF in the extraction agent phase (5.9/0.5=11.8) is about 1.5 times as much as that ratio in the feed mixture (10.0/1.5=6.7). Therefore, a satisfactory separative recovery may be performed by using methyl-1,1,2,3,3,3-hexafluoropropylether and almost complete separation of HFC-245fa may be performed by successive recycling of the extraction agent.

Example 7

Using perfluoro-2-methylpentane (sec-$C_6F_{14}$) as the extraction agent, the present process, the separation of 1,1,1,3,3-pentafluoropropane from the mixture comprising 1,1,1,3,3-pentafluoropropane and hydrogen fluoride is performed in a pilot plant according to the flow chart in FIG. 1.

SUS 316 decanter was used as the separating apparatus 20. In the operation, HFC-245fa containing HF in 50% by mol (flow rate: 11.5 kg/hr) is countercurrently contacted with sec-$C_6F_{14}$ (flow rate: 15 kg/hr) at 20° C. and whole HFC-245fa and HF were liquefied and concentrated. The ratio of HFC-245fa/HF=1.7 was adopted. The contact and separation procedure were performed at a temperature of 20° C. and a pressure of 2 atm, and no gas was withdrawn. Each component passing the conduit 9, 11, 21 and 22 in FIG. 1 is shown in the following Table 7.

TABLE 7

| number of conduit | 9 | 11 | 21 | 22 |
|---|---|---|---|---|
| HFC-245fa | 10.0 | 0.0 | 0.1 | 9.9 |
| HF | 1.5 | 0.0 | 1.4 | 0.1 |
| FPE | 0.0 | 15.0 | 0.1 | 14.9 |
| ratio of HFC-245fa/HF | 6.7 | — | 0.1 | 99 |

According to this example, the obtained result is almost the same as that of example 1 used the same extraction agent in a laboratory scale test. Thus, it may be understand that the present process provides almost the same result independent of the process scale.

The present process does not particularly require use of materials having anti-corrosiveness for the equipment thereof since the present process uses chemicals having no corrosiveness for separation of 1,1,1,3,3-pentafluoropropane from hydrogen fluoride. Therefore, the cost of installation and the cost of measures for safe operation may be reduced than the conventional process.

Further, the purification of 1,1,1,3,3-pentafluoropropane may be effectively performed by the effective separation of 1,1,1,3,3-pentafluoropropane from hydrogen fluoride.

Particularly, when 1,1,1,3,3-pentachloropropane is used as the extraction agent, a third component other than the two components of the starting materials never enters into the reaction system. Therefore, the equipment of the present process does not require a separation measure for removing the third component from both the product phase and the recycle phase, so that costs of installation and operation may be reduced.

What is claimed is:

1. A process of purification of 1,1,1,3,3-pentafluoropropane characterized by contacting at least one extraction agent selected from the group consisting of (a) a fluorohydrocarbon compound corresponds to the general formula (I):

$$C_xF_yH_z \qquad (I)$$

in which x is an integer from 3 to 10, y is an integer from 2 to 22 and z is an integer from 0 to 6;

(b) an amine compound corresponds to the general formula (II):

$$R_1R_2R_3N \qquad (II)$$

in which $R_1$, $R_2$ and $R_3$ are fluoroalkyl groups each having 1–10 carbon atoms, respectively, and $R_1$, $R_2$ and $R_3$ may have at most two hydrogen atoms, respectively;

(c) an ether compound corresponds to the general formula (III):

$$R_4OR_5 \qquad (III)$$

in which $R_4$ and $R_5$ are alkyl groups each having 1–10 carbon atoms, respectively, and at least one of $R_4$ and $R_5$ contains one fluorine atom; and (d) a chlorohydocarbon compound corresponds to the general formula (IV):

$$C_lCl_mH_n \qquad (IV)$$

in which l is an integer from 3 to 10, m is an integer from 2 to 22 and n is an integer from 0 to 6 with a mixture comprising 1,1,1,3,3-pentafluoropropane and hydrogen fluoride so as to form a liquid mixture and separating the liquid mixture into two liquid layers, followed by obtaining an extraction agent layer including 1,1,1,3,3-pentafluoropropane and the extraction agent as the main components, and separatively recovering 1,1,1,3,3-pentafluoropropane from the extraction agent layer.

2. The process according to claim 1 wherein the extraction agent to be used is at least one compound selected from the group consisting of the following (a) to (d):

(a) perfluoro-2-methylpentane, perfluoro-n-hexane, 1,1,1,2,2,3,4,5,5,5-decafluoropentane, perfluoro-2-methyl-2-pentene, perfluoro-4-methyl-2-pentene, ω-H perfluorooctane($C_8F_{17}H$)) and ω-H perfluorohexane;

(b) perfluorotributylamine and perfluorotripentylamine;

(c) methyl-1,1,1,2,3,3-hexafluoropropylether, ethyl-1,1,1,2,3,3-hexafluoropropylether and propyl-1,1,1,2,3,3-hexafluoropropylether, 1-methoxy-nonafluorobutane, and 1-ethoxy-nonafluorobutane; and (d) 1,1,1,3,3-pentachloropropane, hexachloropropane, trichloroethylene, and perchloroethylene.

3. The process according to claim 1 wherein an amount of the extraction agent used in the contacting step is in the range from 0.3 to 30 times as much as an amount of 1,1,1,3,3-pentafluoropropane in a molar ratio.

4. The process according to claim 1 wherein the separating step is performed at a temperature in a range from −30° C. to 100° C. and a pressure in a range from 1 to 30 atm.

5. The process according to claim 1 wherein the mixture comprises HCl and the other fluorohydrocarbon(s).

6. The process according to claim 1 wherein 1,1,1,3,3-pentafluoropropane is separatively recovered by distilling the extraction agent layer, and simultaneously the extraction agent is separated and recycled to the contacting step.

7. The process according to claim 1 wherein the extraction agent and 1,1,1,3,3-pentafluoropropane, or the extraction agent is removed from a layer containing hydrogen fluoride as a main component obtained through separating the resulted mixture into the liquid layers, and the balance is recovered or recycled to a reaction step.

8. The process according to claim 1 wherein a mixture containing 1,1,1,3,3-pentafluoropropane and hydrogen fluoride obtained from the reaction of 1,1,1,3,3-pentachloropropane with hydrogen fluoride is contacted with 1,1,1,3,3-pentachloropropane as the extraction agent so as to form a resulted mixture and the resulted mixture is separated into the two liquid layers; and 1,1,1,3,3-pentafluoropropane is selectively recovered from the extraction agent layer containing the extraction agent and 1,1,1,3,3-pentafluoropropane as the main components; and the layer containing hydrogen fluoride as a main component is recycled to the reaction without removing the extraction agent.

9. The process according to claim 8 wherein, after 1,1,1,3,3-pentafluoropropane is removed, the layer containing hydrogen fluoride as the main component is recycled to the reaction without removing the extraction agent.

* * * * *

UNITED STATES PATENT AND TRADEMARK OFFICE
CERTIFICATE OF CORRECTION

PATENT NO. : 6,191,328 B1
DATED : February 20, 2001
INVENTOR(S) : Keisuke Kitano and Takashi Shibanuma It is certified that error appears in the above-identified patent and that said Letters Patent is hereby corrected as shown below:

<u>Title page, item [54], column 1, lines 1-2,</u>
Change the title from "METHOD FOR 1, 1, 1, 3, 3– PENTAFLUOROPROPANE" to
-- METHOD FOR PURIFYING 1, 1, 1, 3, 3– PENTAFLUOROPROPANE --

Signed and Sealed this

Twenty-fifth Day of September, 2001

Attest:

*Attesting Officer*

NICHOLAS P. GODICI
*Acting Director of the United States Patent and Trademark Office*